(12) United States Patent
Poppinga et al.

(10) Patent No.: US 12,135,396 B2
(45) Date of Patent: Nov. 5, 2024

(54) RADIOTHERAPEUTIC DETECTOR DEVICE

(71) Applicant: PTW—Freiburg Physikalisch-Technische Werkstätten Dr. Pychlau GmbH, Freiburg (DE)

(72) Inventors: Daniela Poppinga, Berlin (DE); Markus Lapp, Denzlingen (DE)

(73) Assignee: PTW-Freiburg Physikalisch—Technische Werkstätten Dr. Pychlau GmbH, Freiburg (DE)

( * ) Notice: Subject to any disclaimer, the term of this patent is extended or adjusted under 35 U.S.C. 154(b) by 206 days.

(21) Appl. No.: 17/668,866

(22) Filed: Feb. 10, 2022

(65) Prior Publication Data

US 2022/0260729 A1 Aug. 18, 2022

(30) Foreign Application Priority Data

Feb. 18, 2021 (DE) .......................... 102021103927.4

(51) Int. Cl.
*G01T 1/02* (2006.01)
*A61B 6/42* (2024.01)
*A61N 5/10* (2006.01)

(52) U.S. Cl.
CPC .............. *G01T 1/02* (2013.01); *A61B 6/4266* (2013.01); *A61N 5/1071* (2013.01); *A61N 5/1075* (2013.01); *A61N 2005/1076* (2013.01)

(58) Field of Classification Search
CPC .. A61B 6/4266; A61N 5/1071; A61N 5/1075; A61N 2005/1076; G01T 1/02
See application file for complete search history.

(56) References Cited

U.S. PATENT DOCUMENTS

| | | | |
|---|---|---|---|
| 9,618,630 B2 | 4/2017 | Kross et al. | |
| 2014/0306117 A1 | 10/2014 | Vacheret et al. | |
| 2015/0177390 A1* | 6/2015 | Mattson | G01T 1/00 250/366 |
| 2017/0059719 A1* | 3/2017 | Kross | G01T 1/20187 |
| 2017/0120076 A1 | 5/2017 | Allinson et al. | |
| 2019/0187302 A1* | 6/2019 | Nelson | G01T 1/20187 |
| 2020/0379134 A1* | 12/2020 | Pola | G01T 3/02 |
| 2023/0248999 A1* | 8/2023 | Eriksson | A61B 6/4233 378/65 |

FOREIGN PATENT DOCUMENTS

IT 201800003885 9/2019

OTHER PUBLICATIONS

Feygelman, V. et al., "Evaluation of a biplanar diode array dosimeter for quality assurance of step-and-shoot IMRT", Journal of Applied Clinical Medical Physics, 10(4), 64-78 (Year: 2009).*

* cited by examiner

*Primary Examiner* — Blake C Riddick
(74) *Attorney, Agent, or Firm* — Volpe Koenig

(57) ABSTRACT

A radiotherapeutic detector device (14) comprising a detector arrangement (1) which has more than two carriers (2) which are arranged crosswise, and a detector field (7) is arranged on each carrier (2).

20 Claims, 3 Drawing Sheets

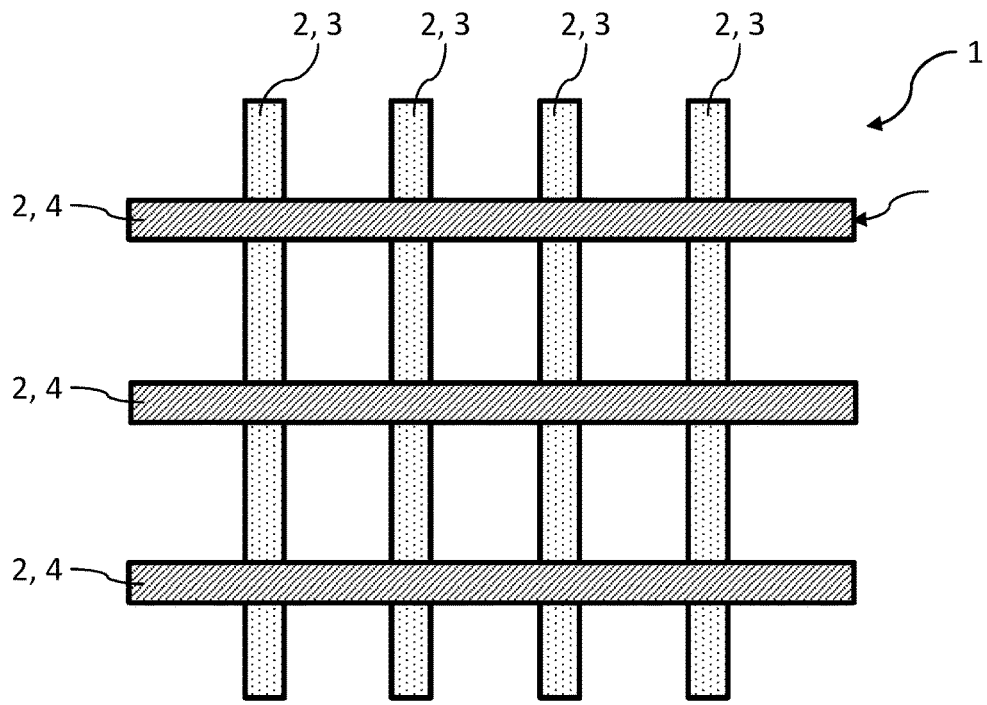
Fig. 1
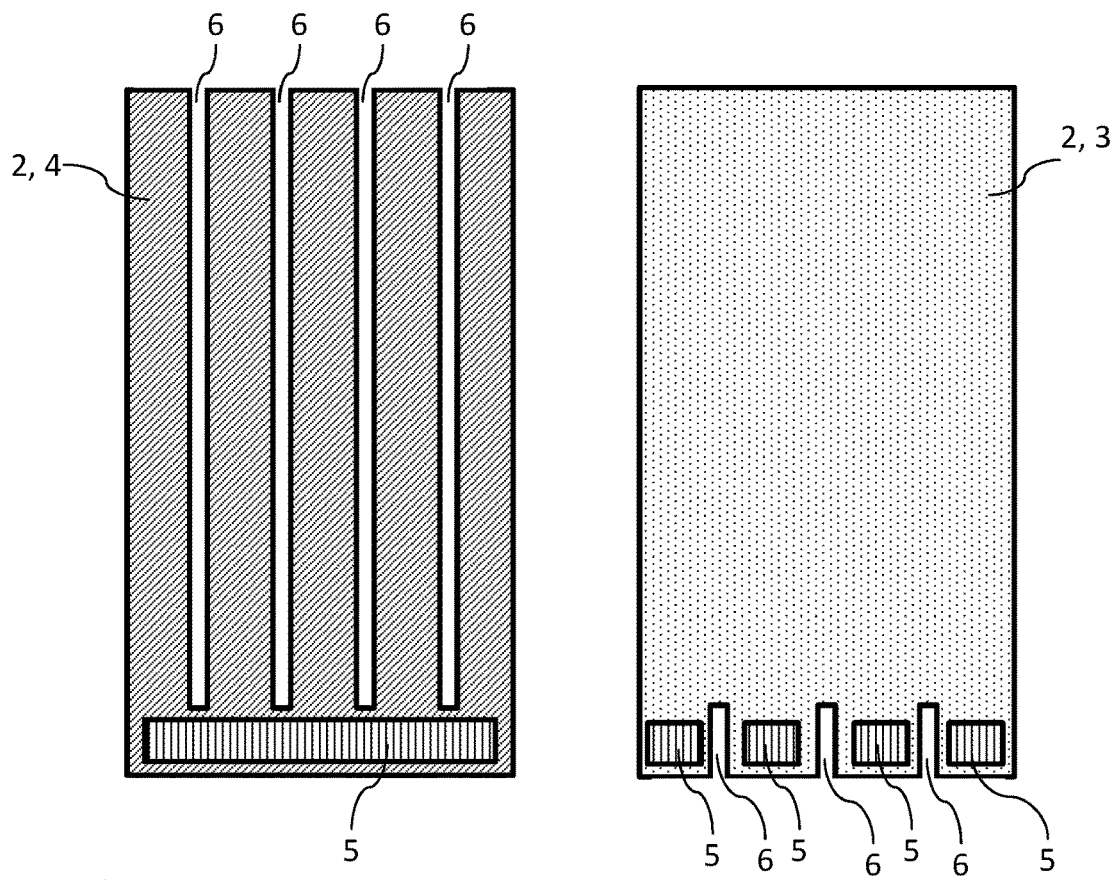
Fig. 2
Fig. 3

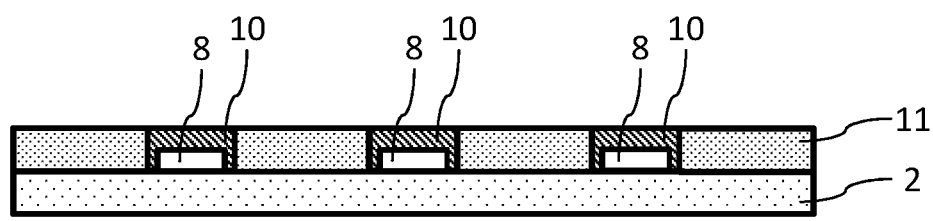
Fig. 5
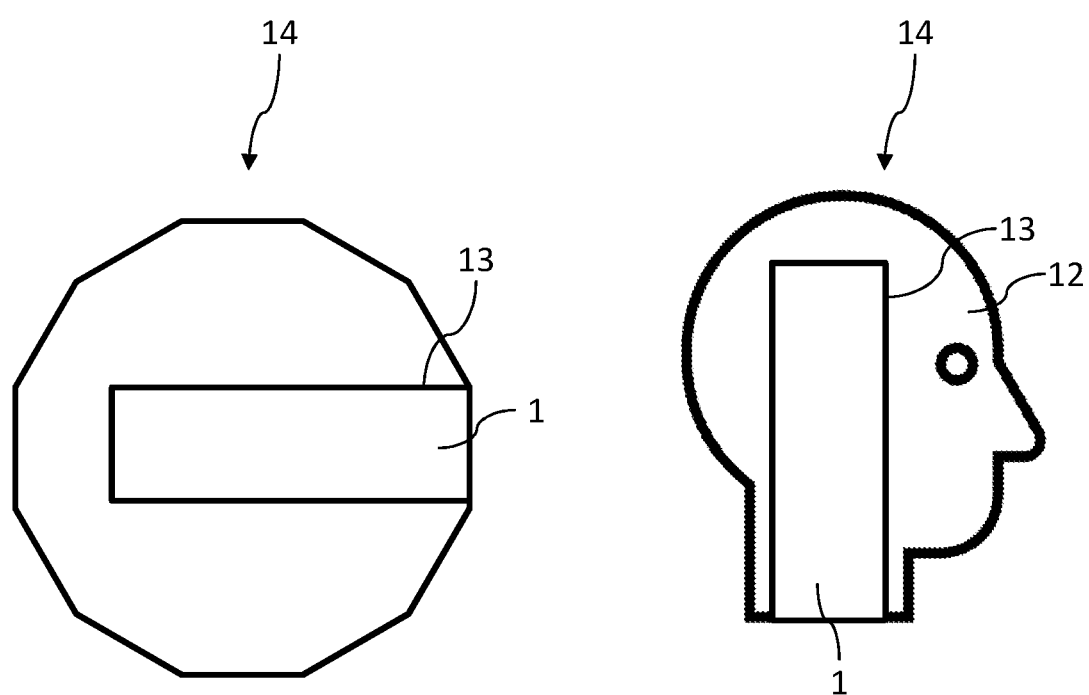
Fig. 6
Fig. 7

RADIOTHERAPEUTIC DETECTOR DEVICE

INCORPORATION BY REFERENCE

The following documents are incorporated herein by reference as if fully set forth: German Patent Application No. 10 2021 103 927.4, filed Feb. 18, 2021.

TECHNICAL FIELD

The invention relates to a radiotherapeutic detector device comprising a detector arrangement.

BACKGROUND

Detector devices comprising a detector arrangement are known per se from the prior art. By way of example, such a detector device can be used in a phantom for determining or verifying a radiation dose or a patient plan. However, the detector device can also be used for gauging, in particular for symmetric characterization and/or constancy testing, of a radiotherapeutic radiation apparatus.

SUMMARY

It is the object of the invention to improve such a detector device.

This object is achieved by a detector device having one or more of the features disclosed herein.

The detector device according to the invention is characterized in that the detector arrangement has more than two carriers which are arranged crosswise, and in that a detector field is arranged on each carrier. A detector arrangement with many detectors can easily be produced in this way. Moreover, the detector arrangement can be more easily adapted to different resolutions and dimensions, for instance by virtue of altering the number of carriers arranged crosswise.

In an embodiment, the detectors of the detector fields are designed to determine the radiation dose of an ionizing radiation, preferably x-ray radiation.

In an embodiment, the carriers each have printed circuit boards. Electrical contacting is easily implementable in this way. In particular, the carrier may be formed by the printed circuit board.

In an embodiment, crossed carriers penetrate one another and/or crossing carriers define a corresponding detection region.

In an embodiment, the crossed carriers are formed in a manner adhesively bonded to one another and/or in a plug-in connected manner and/or in one piece.

In an embodiment, the carriers have an insertion slot which is preferably open on one side and in which another carrier of the more than two carriers is plugged in, in particular by means of an, or its, insertion slot.

It may be particularly advantageous if the carriers are plugged into one another longitudinally with respect to the receiving carrier, that is to say longitudinally with respect to the axis. What this can easily achieve is that the electronics are arranged at a common end of the detector arrangement.

In an embodiment, a mechanical and/or electrical slot is formed on a carrier, another carrier being plugged therein, preferably transversely to the receiving carrier. In this way, the detector arrangement can easily be assembled.

In an embodiment, the more than two carriers form a two-dimensional lattice, in particular made of two crossed assemblages, preferably of carriers aligned parallel to one another.

In an advantageous embodiment, carriers in one alignment of the lattice have long slots which substantially extend over the entire length of the carrier, the carriers each having only a narrow, unslotted region. The crosswise arranged carriers only have short slots; in particular, the slots are matched to the unslotted region of the other carriers so that these can be plugged into one another. This is advantageous in that it is easy to design the distribution of the detectors on the carriers.

Moreover, the unslotted region is located at one end of the detector arrangement, and so electronics arranged on the carriers in this region can easily be protected from radiation without the creation of a dead space, from the direction of which no radiation can be measured.

In an embodiment, the at least two carriers cross at an intersection, the line of intersection being aligned longitudinally with respect to an insertion direction of the insert in particular.

In an embodiment, the carriers are electrically contacted at their end face oriented toward the, or an, insertion direction of the insert.

In an embodiment, the carriers each have a planar embodiment.

In an embodiment, the interstices between the carriers are filled or fillable with a material, the material between the carriers being replaceable in particular. In this way it is possible to set a certain absorption rate, for example an absorption rate similar to that of the human body.

In an embodiment, the detector arrangement is arranged in a phantom, preferably as insert, in particular as an encapsulated insert.

In an embodiment, the phantom has an irregular shape, essentially reproducing or approximating the shape of a human head in particular.

In an embodiment, the phantom has a regular shape, the phantom being formed as rhombicuboctahedron in particular.

In an embodiment, the size of the phantom is matched to the size of a human head.

In an embodiment, the phantom is arranged in the detector device in stationary fashion.

In an embodiment, the phantom has a non-deformable design.

In an embodiment, the phantom has a density similar to that of water and/or an attenuation coefficient similar to that of water.

The invention also comprises a production series of radiotherapeutic detector devices with at least two variants, which each form a radiotherapeutic detector device according to the invention, wherein the at least two variants have different external contours and the detector arrangements, as inserts, have a corresponding design. In this way, a detector arrangement for different purposes can be configured easily and cost-effectively.

The invention also comprises the use of a radiotherapeutic detector device according to the invention for gauging a radiotherapeutic radiation apparatus, in particular for dosimetric characterization and/or a constancy test, and/or for verifying a radiotherapeutic patient plan.

BRIEF DESCRIPTION OF THE DRAWINGS

The invention is explained in more detail below on the basis of preferred exemplary embodiments, with reference being made to the attached drawings, in which:

FIG. 1: shows a front view of a detector arrangement of a detector device according to the invention with crosswise arranged carriers, FIG. 2: shows a carrier with long slots, as is arranged horizontally in FIG. 1, FIG. 3: shows a carrier with short slots, as is arranged vertically in FIG. 1, FIG. 4: shows a carrier with illustrated detectors, FIG. 5: shows a cross section through a carrier with detectors, FIG. 6: shows a detection device according to the invention with a regularly shaped phantom with an insert with a detector arrangement, and FIG. 7: shows a detection device according to the invention with an irregularly shaped phantom with an insert with a detector arrangement.

DETAILED DESCRIPTION

Figure 4:
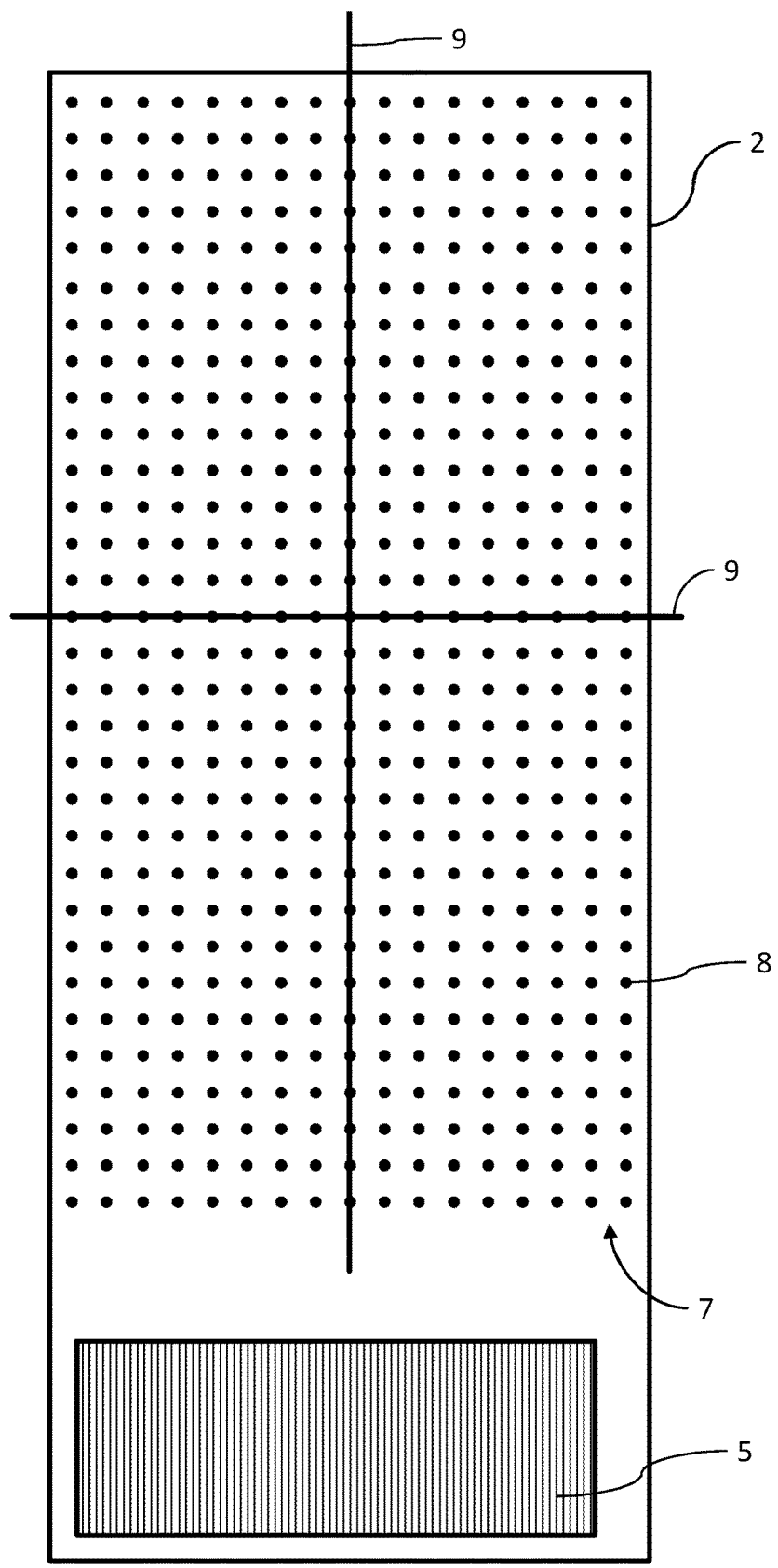

FIG. 1 schematically shows a front view of a detector arrangement 1 of a detector device according to the invention in a longitudinal direction. In the example, the detector arrangement 1 has a total of seven carriers 2 which form a two-dimensional lattice, with four vertical carriers 3 and three horizontal carriers 4 being imaged. In this case, the imaged example only serves for clearer illustration. In practice, a detector arrangement 1 may also have more carriers in both alignments, for example six or more horizontal carriers and five or more vertical carriers. In this case, the number of carriers may depend on the dimensions and the desired accuracy. Likewise, the relative position of the detector device is not fixed, and so the terms vertical and horizontal only serve to explain the imaged example and should not be construed as restrictive in respect of the actual relative position of the carriers. Accordingly, the carriers shown and denoted here as vertical may in fact also be aligned horizontally or diagonally in a detector device. However, the crosswise arrangement of the carriers is important in this case.

In the example, the vertical carriers 3 and the horizontal carriers 4 cross one another at an angle of 90°. However, a different angle may also be chosen.

FIG. 2 shows a plan view of one of the horizontal carriers 4 of FIG. 1.

At one end, the carrier 4 has an electronics region 5, in which for example control and/or evaluation electronics may be arranged.

In the example, the carrier 4 has four insertion slots 6 which are arranged in the longitudinal direction and which essentially extend from the electronics region 5 to the opposite end of the carrier 4. The insertion slots are open at this opposite end so that vertical carriers 3 can be pushed in here. As a result, a crosswise arrangement of the carriers 2 is easily obtained.

The detectors are arranged on the carrier outside of the electronics region 5 but are not shown in this illustration.

FIG. 3 shows a plan view of one of the vertical carriers 3 of FIG. 1.

The carrier 3 has an electronics region 5, the extent of which in the longitudinal direction substantially corresponds to the horizontal carrier 4 of FIG. 2. The vertical carrier 4 likewise has insertion slots 6, but these are open at the end of the carrier 4 with the electronics region 5 and essentially extend over the electronics region 5 in the longitudinal direction. As a result, an insertion slot 6 that is complementary to the horizontal carrier 4 is formed. When a vertical carrier 3 is pushed into a horizontal carrier 4, the insertion slot 6 of the vertical carrier 3 engages over the electronics region 5 of the horizontal carrier 4. Consequently, the electronics regions 5 of the carriers 3 and 4 are located immediately adjacent to one another. As a result, there can be simple contacting of the electronics regions 5 among themselves. By way of example, plug-in connectors can be used to this end.

A further advantage of this arrangement arises from the fact that all of the electronics are arranged in the electronics regions 5 at one end of the detector device 1. In this way, it is easily possible to protect the electronics from the radiation, for example by virtue of this electronics region 5 being arranged outside of a radiation region.

Deviating from the embodiments shown here, the insertion slots of the carriers may also be symmetric, that is to say have approximately the same lengths in the horizontal carriers 4 and in the vertical carriers 3, or have other deviating length ratios.

FIG. 4 schematically shows a carrier 2 with a detector field 7. No insertion slots are illustrated in this illustration. The carrier 2 shown can be a vertical carrier 3 or a horizontal carrier 4, wherein provision should be made in each case of insertion slots 6 corresponding to those in FIG. 2 or FIG. 3, or of other insertion slots.

The detector field 7 has a plurality of detectors 8 which are arranged in a regular grid that is aligned along the two principal axes 9 of the carrier. In the example, the detector field 7 respectively has 17 detectors 8 in the transverse direction and respectively has 31 detectors 8 in the longitudinal direction, that is to say a total of 527 detectors. Accordingly, the detector field 7 has a very high number of detectors 8. In particular, this is rendered possible due to the fact that the control electronics required to this end are arranged in the electronics region directly on the carrier 2. In particular, it is advantageous if the detectors 8 are arranged with a raster spacing of 5 mm from one another. As a result, a high resolution of the measurement can be attained, as a result of which even the treatment of lesions with dimensions of the order of 10 mm can be verified with sufficient accuracy.

FIG. 5 shows a portion of a cross section of the carrier 2 of FIG. 4. In the example, the carrier 2 is in the form of a multilayer printed circuit board such that electronic components, for instance in the electronics region 5, and the detectors 8 may be arranged directly on the carriers 2.

In the example, the detectors 8 are diodes which are arranged directly on the carrier 2 without an own housing. In this case, electrical contacting of the diodes is implemented by wire bonding and possibly by a conductive paste on the lower side of the diodes. The detectors 8 are encapsulated by a potting compound 10 in order to protect the sensitive bond wires. A filling material 11 is arranged between the detectors 8 such that the potting compound 10 need not be applied over the whole surface of the carrier 2. The potting compound 10 and the filling material 11 form a plane surface.

The width of the insertion slots 6 therefore substantially corresponds to the overall thickness of the carriers 2 including the filling material 11.

FIG. 6 shows a first embodiment of a detector device 14 according to the invention with a regularly shaped phantom 12. The phantom 12 has an insert 13, into which for example a detector arrangement 1 with crossed carriers 2 as described above is insertable or inserted.

FIG. 7 shows a second embodiment of a detector device 14 according to the invention with a phantom 12, which is modeled on a human head. This phantom 12 likewise has an insert 13 for a detector arrangement.

It is particularly advantageous if the phantoms 12 of the first and second embodiment have corresponding inserts 13 such that, as a result, a production series of radiotherapeutic detector devices 14 with at least two variants is formed, which each form a radiotherapeutic detector device 14 according to the invention.

LIST OF REFERENCE SIGNS

1 Detector arrangement
2 Carrier
3 Vertical carrier
4 Horizontal carrier
5 Electronics region
6 Insertion slot
7 Detector field
8 Detector
9 Main axis
10 Potting compound
11 Filling material
12 Phantom
13 Insert
14 Detector device

The invention claimed is:

1. A radiotherapeutic detector device (14), comprising:
a detector arrangement (1) including more than two carriers (2) which are arranged crosswise,
a detector field (7) arranged on each of the carriers (2), wherein detectors (8) of the detector fields (7) are configured to detect photons, and
crossed ones of the carriers (2) penetrate one another.

2. The radiotherapeutic detector device (14) as claimed in claim 1, wherein the detectors (8) of the detector fields (7) are configured to determine a radiation dose of X-ray radiation.

3. The radiotherapeutic detector device (14) as claimed in claim 1, wherein the carriers (2) each include printed circuit boards.

4. The radiotherapeutic detector device (14) as claimed in claim 1, wherein crossed ones of the carriers (2) define a corresponding detection region.

5. The radiotherapeutic detector device (14) as claimed in claim 1, wherein crossed ones of the carriers (2) are at least one of adhesively bonded to one another, plug-in connected, or formed in one piece.

6. The radiotherapeutic detector device (14) as claimed in claim 1, wherein the carriers (2) have an insertion slot (6) which is open on one side and in which another one of the carriers (2) is plugged in longitudinally with respect to a receiving one of the carriers (2).

7. The radiotherapeutic detector device (14) as claimed in claim 1, wherein the more than two carriers (2) form a two-dimensional lattice made of two crossed assemblages.

8. The radiotherapeutic detector device (14) as claimed in claim 1, wherein the at least two carriers (2) cross at an intersection, a line of contact between the at least two carriers being aligned longitudinally with respect to an insertion direction of an insert by which one of the carriers is plugged into another one of the carriers (2).

9. The radiotherapeutic detector device (14) as claimed in claim 8, wherein the carriers (2) are electrically contacted at end faces thereof oriented toward the insertion direction of the insert.

10. The radiotherapeutic detector device (14) as claimed in claim 1, wherein the carriers (2) are each planar.

11. The radiotherapeutic detector device (14) as claimed in claim 1, wherein interstices between the carriers (2) are filled or fillable with a material.

12. The radiotherapeutic detector device (14) as claimed in claim 1, wherein the detector arrangement (1) is arranged in a phantom (12).

13. The radiotherapeutic detector device (14) as claimed in claim 12, wherein the phantom (12) has an irregular shape.

14. The radiotherapeutic detector device (14) as claimed in claim 12, wherein the phantom (12) has a regular shape.

15. The radiotherapeutic detector device (14) as claimed in claim 12, wherein a size of the phantom (12) is matched to a size of a human head.

16. The radiotherapeutic detector device (14) as claimed in claim 12, wherein the phantom (12) is arranged in the detector device in stationary fashion.

17. The radiotherapeutic detector device (14) as claimed in claim 12, wherein the phantom (12) has a non-deformable design.

18. The radiotherapeutic detector device (14) as claimed in claim 12, wherein the phantom (12) has at least one of a density or an attenuation coefficient similar to that of water.

19. A production series of radiotherapeutic detector devices (14) with at least two variants, which each form the radiotherapeutic detector device (14) as claimed in claim 1, wherein the at least two variants have different external contours and the detector arrangements (1), as inserts (13), have a corresponding design.

20. A method for gauging a radiotherapeutic radiation apparatus, the method including providing the radiotherapeutic detector device (14) as claimed in claim 1, and using the radiotherapeutic radiation apparatus for at least one of dosimetric characterization, constancy testing, or verifying a radiotherapeutic patient plan.

* * * * *